United States Patent
Shin et al.

(10) Patent No.: US 8,775,186 B2
(45) Date of Patent: Jul. 8, 2014

(54) METHOD FOR EMOTION COMMUNICATION BETWEEN EMOTION SIGNAL SENSING DEVICE AND EMOTION SERVICE PROVIDING DEVICE

(75) Inventors: Hyun Soon Shin, Daejeon (KR); Sung Won Lee, Gyeonggi-do (KR); Choong Seon Hong, Gyeonggi-do (KR)

(73) Assignee: Electronics and Telecommnications Research Institute, Daejeon (KR)

( * ) Notice: Subject to any disclaimer, the term of this patent is extended or adjusted under 35 U.S.C. 154(b) by 364 days.

(21) Appl. No.: 12/981,208

(22) Filed: Dec. 29, 2010

(65) Prior Publication Data

US 2011/0172992 A1   Jul. 14, 2011

(30) Foreign Application Priority Data

Jan. 8, 2010   (KR) .................. 10-2010-0001924

(51) Int. Cl.
  *G10L 11/00* (2006.01)
  *H04L 1/00* (2006.01)
(52) U.S. Cl.
  USPC ...... 704/270.1; 704/201; 714/748; 455/414.1
(58) Field of Classification Search
  CPC ......... G10L 25/63; G10L 19/005; H04L 1/00; A61B 5/0004
  USPC .............. 704/231, 270, 270.1, 201; 714/748, 714/749, 750, 751; 455/414.1
  See application file for complete search history.

(56) References Cited

U.S. PATENT DOCUMENTS

| | | | |
|---|---|---|---|
| 8,041,344 B1 * | 10/2011 | Coughlan et al. .......... | 455/414.1 |
| 8,220,042 B2 * | 7/2012 | Hagiu et al. .................... | 726/14 |
| 8,285,257 B2 * | 10/2012 | Isobe et al. .................. | 455/412.2 |
| 2003/0182123 A1 * | 9/2003 | Mitsuyoshi .................... | 704/270 |
| 2003/0233457 A1 * | 12/2003 | Basilier et al. ................ | 709/227 |
| 2004/0147814 A1 * | 7/2004 | Zancho et al. ................ | 600/300 |
| 2006/0036741 A1 * | 2/2006 | Kiss et al. ..................... | 709/227 |
| 2006/0122834 A1 * | 6/2006 | Bennett ......................... | 704/256 |
| 2006/0154603 A1 * | 7/2006 | Sachs et al. ..................... | 455/39 |
| 2008/0059158 A1 * | 3/2008 | Matsuo et al. ................ | 704/221 |
| 2009/0177607 A1 * | 7/2009 | Matsushima ................. | 709/206 |
| 2009/0285141 A1 * | 11/2009 | Cai et al. ....................... | 370/311 |
| 2010/0003969 A1 * | 1/2010 | Isobe et al. .................. | 455/412.1 |
| 2010/0099955 A1 * | 4/2010 | Thomas et al. ............... | 600/300 |
| 2010/0217595 A1 * | 8/2010 | Kim et al. ..................... | 704/250 |
| 2010/0240416 A1 * | 9/2010 | Knight .......................... | 455/566 |
| 2011/0137137 A1 * | 6/2011 | Shin et al. ..................... | 600/301 |
| 2011/0143728 A1 * | 6/2011 | Holopainen et al. ....... | 455/414.1 |

(Continued)

FOREIGN PATENT DOCUMENTS

KR   10-2006-0124082 A   12/2005
KR   2008-0067854 A   7/2008

(Continued)

*Primary Examiner* — Martin Lerner
(74) *Attorney, Agent, or Firm* — Rabin & Berdo, P.C.

(57) ABSTRACT

Provided are a method for emotion communication to share a user's emotions between an emotion signal sensing device and an emotion service providing device. The method for emotion communication includes: the emotion signal sensing device's sensing biological and environmental information of the user and generating an emotion signal and emotion information of the user based on the biological and environmental information; establishing an emotion communication connection with the emotion service providing device; transmitting the emotion signal and the emotion information to the emotion service providing device by the emotion communication connection establishment; and breaking the connection with the emotion service providing device.

9 Claims, 11 Drawing Sheets

(56) References Cited

U.S. PATENT DOCUMENTS

2011/0144452 A1* 6/2011 Shin et al. ............... 600/300
2011/0207100 A1* 8/2011 Brokken et al. ............ 434/236
2012/0308971 A1* 12/2012 Shin et al. ............... 434/236
2013/0275048 A1* 10/2013 Hong et al. ............... 702/19

FOREIGN PATENT DOCUMENTS

| KR | 10-2008-0106830 A | | 12/2008 |
|---|---|---|---|
| KR | 2009-0003521 A | | 1/2009 |
| WO | WO 2008/113947 | * | 9/2008 |
| WO | WO-2008/150062 A1 | | 12/2008 |

* cited by examiner

METHOD FOR EMOTION COMMUNICATION BETWEEN EMOTION SIGNAL SENSING DEVICE AND EMOTION SERVICE PROVIDING DEVICE

CROSS-REFERENCE TO RELATED APPLICATION

This application claims priority to and the benefit of Korean Patent Application No. 10-2010-0001924 filed in the Korean Intellectual Property Office on Jan. 8, 2010, the entire contents of which are incorporated herein by reference.

BACKGROUND OF THE INVENTION (a) Field of the Invention

The present invention relates to a method for emotion communication between an emotion signal sensing device and an emotion service providing device.

(b) Description of the Related Art

As society is moving toward personalization and aging, emotion-based services for emotion communication are required. Accordingly, studies on the recognition of emotions of a user and the provision of an emotion-based service desired by the user are actively being pursued.

Although studies on a standardized protocol for sending and receiving an emotion signal are being carried out to allow an emotion signal sensing device that senses a user's emotions and an emotion service providing device that provides the user with an emotion service to share information about the user's emotions, these studies have not yet been put into practice.

Hence, there is a need for a practical standard protocol for sending and receiving an emotion signal.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a method for emotion communication to share a user's emotions between an emotion signal sensing device and an emotion service providing device.

According to one exemplary embodiment of the present invention, there is provided a method for emotion communication of an emotion signal sensing device that senses a user's emotions, the method including: sensing biological and environmental information of the user by the emotion signal sensing device; generating an emotion signal and emotion information of the user based on the biological and environmental information; establishing an emotion communication connection with the emotion service providing device; and transmitting the emotion signal and the emotion information to the emotion service providing device by the emotion communication connection establishment.

According to one exemplary embodiment of the present invention, there is provided a method for emotion communication of an emotion service providing device, the method including: receiving a first message requesting emotion communication connection establishment from an emotion signal sensing device; transmitting a second message to the emotion signal sensing device in response to the first message; receiving a third message from the emotion signal sensing device in response to the second message and establishing an emotion communication connection; and receiving an emotion signal and emotion information from the emotion signal sensing device by the emotion communication connection establishment.

According to one exemplary embodiment of the present invention, there is provided a method for emotion communication using a protocol layer for emotion communication between an emotion signal sensing device and an emotion service providing device, wherein the protocol layer includes: a first layer that process an emotion signal and emotion information in order to transmit the same to the emotion service providing device; a second layer that receives the processed emotion signal and emotion information from the first layer, and transmits the processed emotion signal and emotion information to the emotion service providing device; and a protocol management plane that manages a first protocol for transmitting the processed emotion signal and emotion information to the emotion service providing device and a second protocol for establishing a connection between the emotion signal sensing device and the emotion service providing device.

There is proposed a method for emotion signal transmission and reception between an emotion signal sensing device and an emotion service providing device. Therefore, a user can be provided with an emotion-based service desired by the user.

DETAILED DESCRIPTION OF THE EMBODIMENTS

Figure 1:
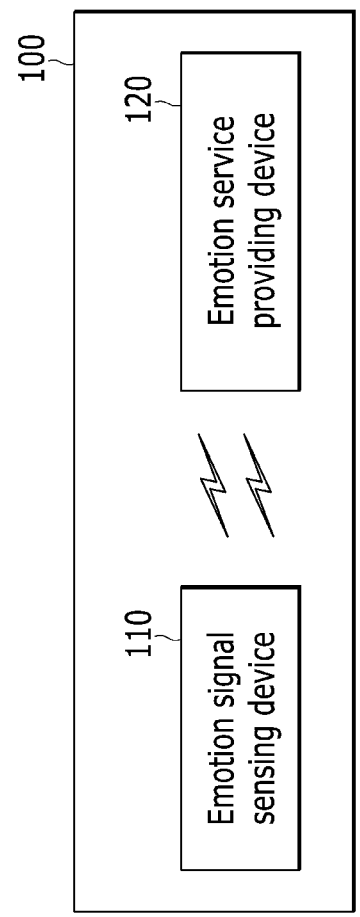
FIG. 1 is a view showing an emotion signal communication system according to one exemplary embodiment of the present invention.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

Throughout the specification, unless explicitly described to the contrary, the word "comprise" and variations such as "comprises" or "comprising" will be understood to imply the inclusion of stated elements but not the exclusion of any other elements.

Throughout the specification, the term "emotion signal" refers to a signal that the emotion signal sensing device generates by sensing and processing a user's emotions.

The term "emotion information" refers to information about a user's emotions extracted from an emotion signal. The term "emotion information" may refer to information about a user's joy, pleasure, sadness, fear, horror, etc. For example, the term "emotion information" may refer to a degree of joy, pleasure, etc. of a user.

In this specification, the term "emotion signal information" can be used to refer to "emotion signal and/or emotion information".

The term "emotion communication" refers to a process for sending and receiving an emotion signal and/or emotion information.

FIG. 1 is a view showing an emotion signal communication system 100 according to one exemplary embodiment of the present invention.

Referring to FIG. 1, the emotion signal communication system 100 includes an emotion signal sensing device 110 and an emotion service providing device 120. The emotion signal sensing device 110 senses a user's biological state or an environmental condition around the user and generates an emotion signal and/or emotion information, and transmits the generated emotion signal and/or emotion information to the emotion service providing device 120. The emotion signal sensing device 110 may be attached to the user's body or located around the user to sense an emotion signal. The emotion service providing device 120 is located locally or remotely from the user, and provides an emotion service to the user based on a signal received from the emotion signal sensing device 110. The emotion service providing device 120 may include, for example, a personal digital assistant (PDA), a mobile phone, a personal computer (PC), etc. Emotion signal transmission and reception between the emotion signal sensing device 110 and the emotion service providing device 120 can be performed, for example, through Bluetooth-based wireless communication.

Figure 2:
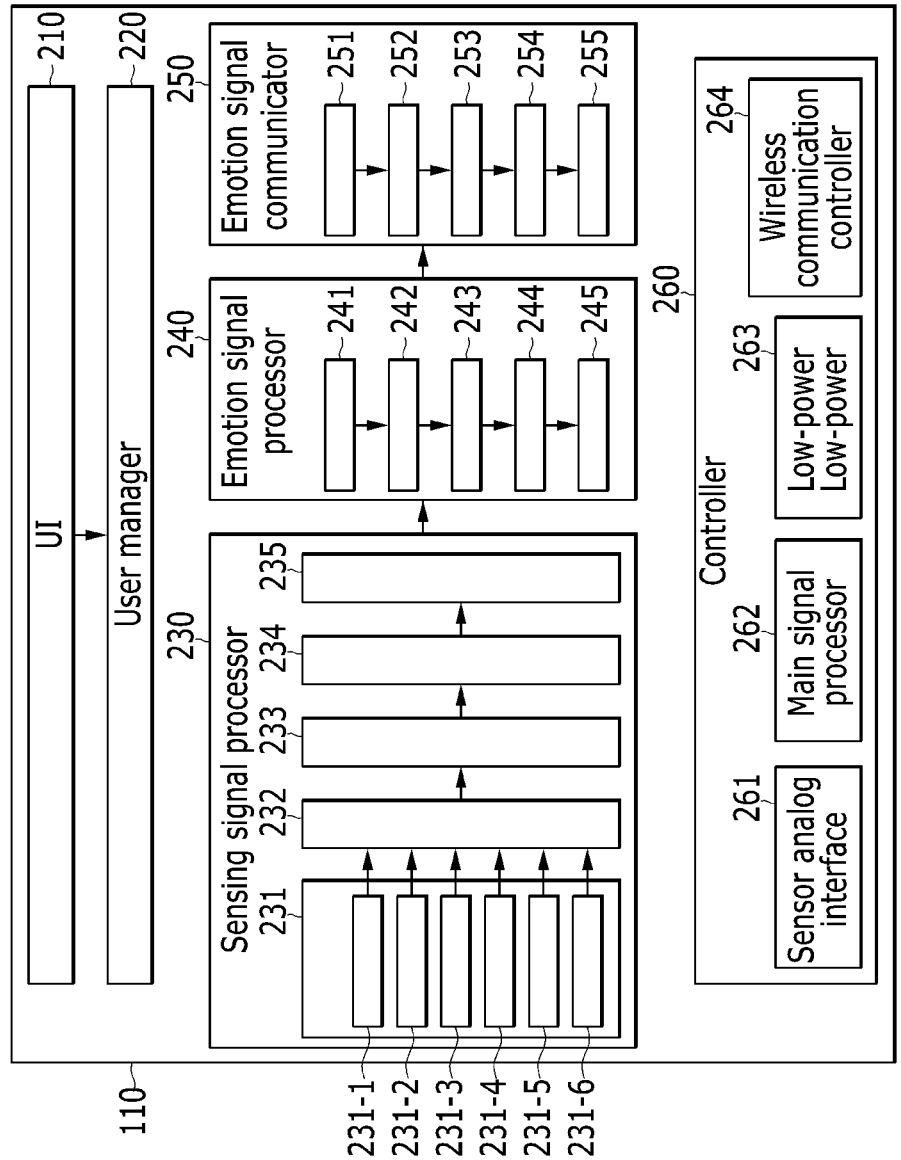
FIG. 2 is a view showing a structure of an emotion signal sensing device according to one exemplary embodiment of the present invention.

FIG. 2 is a view showing a structure of the emotion signal sensing device 110 according to one exemplary embodiment of the present invention.

Referring to FIG. 2, the emotion signal sensing device 110 includes a user interface (UI) 210, a user manager 220, a sensing signal processor 230, an emotion signal processor 240, an emotion signal communicator 250, and a controller 260.

The user interface 210 is means for the user to access the emotion signal sensing device 110, and includes, for example, a keypad, a touchpad, a microphone, etc.

The user manager 220 stores and manages the user's information. For instance, the user's information may include the user's name, gender, age, occupation, preferences, etc.

The sensing signal processor 230 processes a signal sensed from the user, and includes a sensor part 231, an amplifier part 232, a noise removing part 233, an analog to digital (ND) converter part 234, and an output part 235. The sensor part 231 includes a photoplethymography (PPG) sensor 231-1 for extracting information relating to heartbeat by an optical detector, a galvanic skin response (GSR) sensor 231-2 for sensing an electrodermal response, a temperature sensor 231-3 for sensing a body temperature of the user or a surrounding temperature, an acceleration sensor 231-4 for sensing the motion of the user, a voice sensor 231-5, and an infrared sensor 231-6. The amplifier part 232 amplifies a signal sensed by the sensor part 231. The noise removing part 233 removes noise from the signal amplified by the amplifier part 232. The ND converter part 234 converts an analog signal to a digital signal. The output part 235 outputs the digital signal converted by the ND converter part 234.

The emotion signal processor 240 generates an emotion signal and/or emotion information from the signal received from the sensing signal processor 230. The emotion signal processor 240 includes an emotion signal threshold generation/control part 241, an emotion signal extraction part 242, an emotion signal error recognition part 243, an emotion signal error compensation part 244, and an emotion index estimation part 245. The emotion signal threshold generation/control part 241 generates and controls a threshold value for detecting emotion changes. The threshold value may be an average threshold value, or may vary from user to user. For instance, the threshold value may be reset depending on a user's choice based on a user response signal to the provision of an emotion service from the emotion service providing device and information fed back as a result of emotion signal transmission and reception with the emotion service providing device. The emotion signal extraction part 242 extracts an emotion signal based on the threshold value generated/controlled by the emotion signal threshold generation/control part 241. For instance, a signal having a value greater than the threshold value, among the signals output from the sensing signal processor 230, can be extracted as an emotion signal by the emotion signal extraction part 240. The emotion signal error recognition part 243 checks whether the emotion signal extracted by the emotion signal extraction part 242 has an error. For instance, if the signal extracted as the emotion signal is a signal having no effect on emotions in consideration of time or status information, or is far out of a reference range, it can be determined that an error has been generated in the emotion signal. If the emotion signal error recognition part 243 determines that the emotion signal has an error, the emotion signal error compensation part 244 compensates for the error in the emotion signal. For instance, only values before error occurrence or both of values before error occurrence and values after error occurrence can be used (e.g., averaged) for compensation. The emotion index estimation part 245 estimates the emotion index of the user by using the emotion signal. For instance, the emotion index is one example of emotion information.

The emotion signal communicator 250 performs processing for emotion communication between the emotion signal sensing device 110 and the emotion service providing device 120. The emotion signal communicator 250 includes an emotion signal information management part 251, an emotion signal information processing part 252, an emotion communication security processing part 253, an emotion communication protocol processing part 254, and an emotion communication adaptation part 255. The emotion signal information management part 251 manages an emotion signal generated from the emotion signal processor 240 and information fed back from the emotion service providing device. The emotion signal information processing part 252 converts/processes the emotion signal generated from the emotion signal processor 240 and the emotion information in various predefined data formats. The emotion communication security processing part 253 performs security processing for ensuring personal privacy in the course of communicating with the emotion service providing device. For instance, the emotion communication security processing part 253 can encrypt the emotion signal and the emotion information. The emotion communication protocol processing part 254 generates data and a control signal according to a set protocol in order to perform communication with the emotion service providing device. The emotion communication adaptation part 255 adapts the emotion signal in order to perform communication with the emotion service providing device. As the communication technology to be applied varies depending on communication channels, a signal has to be adapted to a channel (e.g., wired or wireless channel) for transmission. For instance, the emotion communication adaptation part 255 can modulate the emotion signal in accordance with a predefined modulation scheme, or amplify the emotion signal.

The controller 260 controls the emotion signal sensing device 110. The controller 260 includes a sensor analog interface 261, a main signal processor 262, a low-power controller 263, and a wireless communication controller 264. The sensor analog interface 261 receives an analog signal from various sensors 231-1, 231-2, 231-3, 231-4, 231-5, and 231-6 of the sensor part 231. The main signal processor 262 boots the emotion signal sensing device 110, and executes a software module. The low-power controller 263 controls the emotion signal sensing device 110 so as to perform low-power operation. The wireless communication controller 264 performs wireless communication protocol connection/transmission/disconnection so as to transmit the emotion signal and the emotion information to the emotion service providing device through wireless communication.

Figure 3:
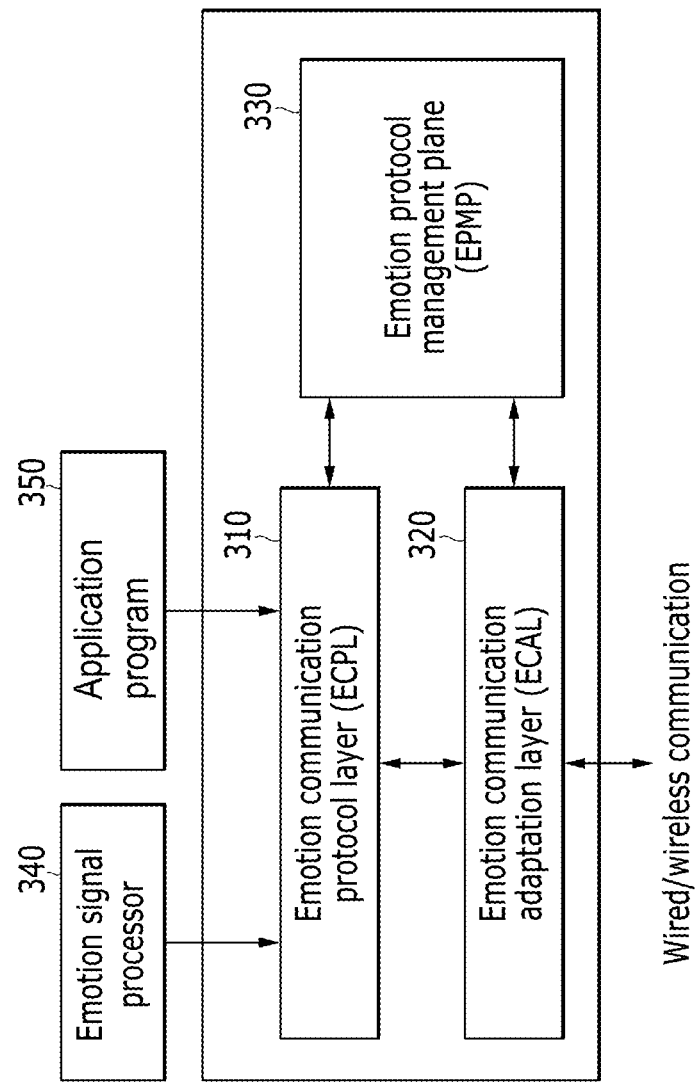
FIG. 3 is a view illustrating a protocol layer structure for emotion communication according to one exemplary embodiment of the present invention.
Figure 4:
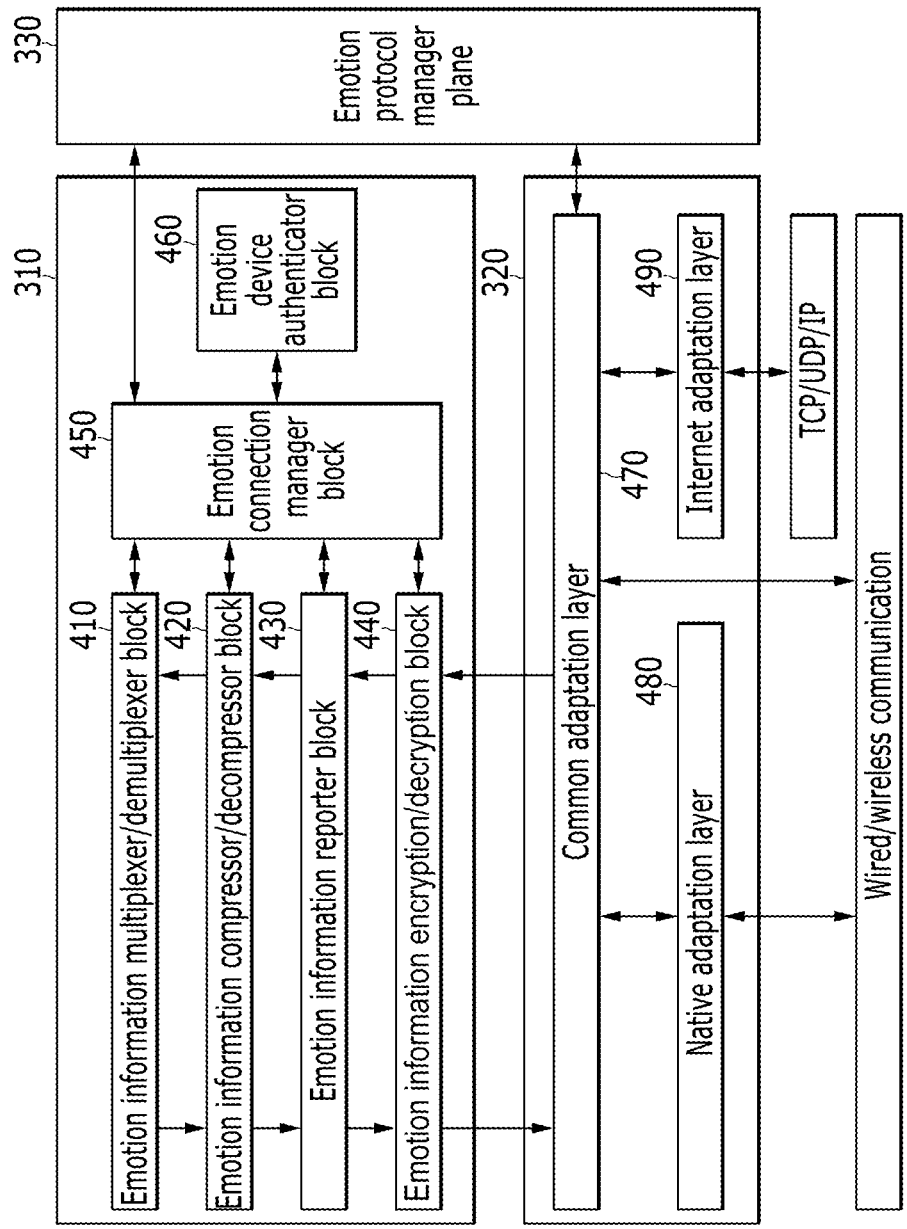
FIG. 4 is a view showing in detail the protocol layer structure for emotion communication illustrated in FIG. 3.

FIG. 3 is a view illustrating a protocol layer structure for emotion communication according to one exemplary embodiment of the present invention, and FIG. 4 is a view showing the protocol layer structure for emotion communication illustrated in FIG. 3 in detail. The protocol layer structure of FIGS. 3 and 4 can be implemented by the emotion signal communicator 250 of FIG. 2.

Referring to FIG. 3, the protocol layer structure for emotion communication includes an emotion communication protocol layer (ECPL) 310, an emotion communication adaptation layer (ECAL) 320, and an emotion protocol management plane (EPMP) 330. The ECPL 310 processes the emotion signal and/or emotion information transferred from the emotion signal processor 340 and transmits it to the ECAL 320. Moreover, the ECPL 310 is connected to an application program 350 to provide the emotion signal and/or the emotion information to the application program. The ECAL 320 transmits the emotion signal and/or emotion information received from the ECPL 310 to the emotion service providing device through wired or wireless communication. Further, the ECAL 320 receives feedback information of the emotion service providing device through wired or wireless communication, and forwards it to the ECPL 310. The ECAL 320 supports low-power operation. The EPMP 330 maintains and manages profile information of a protocol for emotion communication.

More specifically, referring to FIG. 4, the ECPL 310 further includes an emotion information multiplexer/demultiplexer (EImux) block 410, an emotion information compressor/decompressor (EIcomp) block 420, an emotion information reporter (EIR) block 430, an emotion information encryption/decryption (EIcipher) block 440, an emotion connection manager (ECM) block 450, and an emotion device authenticator block 460. The emotion information compressor/decompressor block 420 compresses or decompresses a multiplexed emotion signal and/or emotion information. The emotion information reporter block 430 performs communication between the emotion signal sensing device and the emotion service providing device, and detects and corrects an error that may occur during communication and a resultant loss of the emotion signal and/or emotion information. The emotion information encryption/decryption block 440 encrypts and decrypts the emotion signal and/or emotion information. The emotion connection manager block 450 is connected to the emotion information multiplexer/demultiplexer block 410, the emotion information compressor/decompressor block 420, the emotion information reporter block 430, and the emotion information encryption/decryption block 440, and performs emotion communication connection establishment and termination. The emotion device authenticator block 460 authenticates an emotion communication protocol between the emotion signal sensing device and the emotion service providing device.

The ECAL 320 includes a common adaptation layer (CAL) 470, a native adaptation layer (NAL) 480, and an Internet adaptation layer (IAL) 490. The CAL 470 forwards the emotion signal and/or emotion information received from the ECPL 310 to the NAL 480 or the IAL 490, or directly transmits them to the emotion service providing device through wired or wireless communication. The NAL 480 transmits the emotion signal and/or emotion information received from the CAL 470 to the emotion service providing device through wired or wireless communication. The IAL 490 transmits the emotion signal and/or emotion information received from the CAL 470 to the emotion service providing device through wired or wireless communication via an Internet protocol.

For convenience of explanation, the description focuses on transmitting an emotion signal and/or emotion information to the emotion service providing device by using the protocol layer structure of FIG. 4, but the protocol layer structure of FIG. 4 may also be applied to the case where the emotion service providing device transmits feedback information to the emotion signal sensing device.

Figure 5:
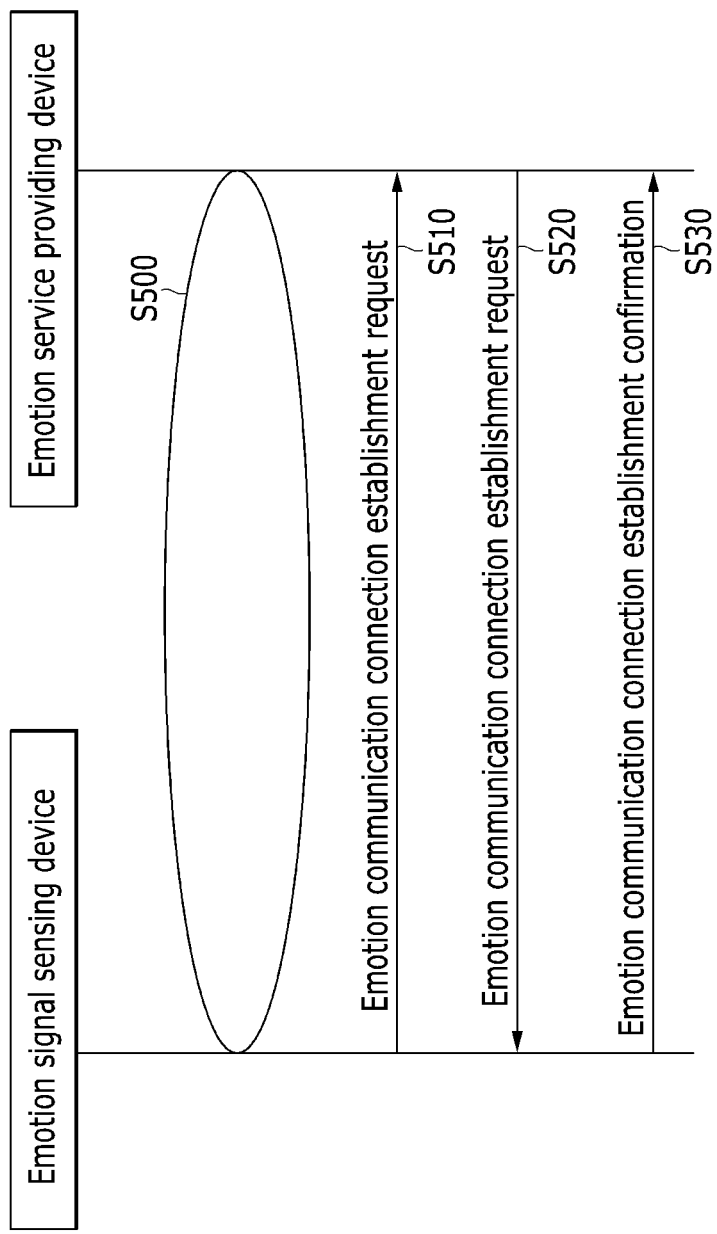
FIG. 5 is a flowchart showing a method of establishing an emotion communication connection between an emotion signal sensing device and an emotion service providing device according to one exemplary embodiment of the present invention.

FIG. 5 is a flowchart showing a method of establishing an emotion communication connection between an emotion signal sensing device and an emotion service providing device according to one exemplary embodiment of the present invention.

Referring to FIG. 5, a protocol connection is established for wireless communication in a general physical layer between the emotion signal sensing device and the emotion service providing device (S500). At this point, a communication protocol connection can be established in a wired or wireless fashion.

The emotion signal sensing device transmits an EC_ConnectionEstablishment_Request message to the emotion service providing device (S510). The EC_ConnectionEstablishment_Request message contains information on the functions and parameters supported by the emotion signal sensing device.

The emotion service providing device transmits an EC_ConnectionEstablishment_Response message to the emotion signal sensing device in response to the EC_ConnectionEstablishment_Request message received from the emotion signal sensing device (S520). The EC_ConnectionEstablishment_Response message may contain information on at least one function and parameter selected from among the functions and parameters contained in the EC_ConnectionEstablishment_Response message.

The emotion signal sensing device determines to communicate with the emotion service providing device based on the function and parameter selected in the EC_ConnectionEstablishment_Response message, and transmits an EC_ConnectionEstablishment_Confirm message to the emotion service providing device (S530). For instance, the EC_ConnectionEstablishment_Confirm message may have the same content as the EC_ConnectionEstablishment_Response message.

Meanwhile, if the emotion signal sensing device determines that there is a problem in performing emotion communication using the function and parameter selected in the EC_ConnectionEstablishment_Response message, the emotion signal sensing device may include information indicating that connection establishment is not possible in the EC_ConnectionEstablishment_Confirm message and transmit it to the emotion service providing device, and break the connection.

Table 1 is one example of the EC_ConnectionEstablishment_Request message, Table 2 is one example of the EC_ConnectionEstablishment_Response message, Table 3 is one example of the EC_ConnectionEstablishment_Confirm message, and Table 4 is one example of the common header of each message.

TABLE 1

| Field Name | Size (Octet) | Default Value | Meaning | |
|---|---|---|---|---|
| Common Message Header included | | | | |
| Flag_CRC_Enabled | 1 | 0 | 0 | Message CRC field disabled |
| | | | 1 | Message CRC field enabled (CRC field included) |
| Flag_Compression_Enabled | 1 | 0 | 0 | Compression of sensing information disabled |
| | | | 1 | Compression of sensing information enabled (EIcomp activated) |
| Flag_Encryption_Enabled | 1 | 0 | 0 | Encryption of sensing information disabled |
| | | | 1 | Encryption of sensing information enabled (EIcipher activated) |
| Flag_Multiplexer_Enabled | 1 | 0 | 0 | Multiplexing of sensing information disabled |
| | | | 1 | Multiplexing of sensing information enabled (EImux activated) |
| Flag_Authentication_Enabled | 1 | 0 | 0 | Authentication of sensing/mobile device disabled |
| | | | 1 | Authentication of sensing/mobile device enabled (EDA activated) |
| Flag_CommonAL_Enabled | 1 | 0 | 0 | Common Adaptation Layer disabled |
| | | | 1 | Common Adaptation Layer enabled (CAL activated) |
| Flag_EIRrexmit_Enabled | 1 | 0 | 0 | Retransmission of sensing information disabled |
| | | | 1 | Retransmission of sensing information enabled (Rexmit supported) |
| Conf_Sampling_Interval | 4 | 10 | | 10 ms × Conf_Sampling_Interval |
| Conf_Samplling_Size | 1 | 4 | 3 | 8 bit/sample |
| | | | 4 | 16 bit/sample |
| | | | 5 | 32 bit/sample |
| Conf_AdaptationLayer_Type | 1 | 0 | 0 | Blank (Direct communication between EIR and COL) |
| | | | 1 | Native Adaptation Layer selected (NAL activated) |
| | | | 2 | Internet Adaptation Layer selected (IAL activated) |
| Conf_Compression_Type | 1 | 0 | 0 | Sampled information only (intra coding) |
| | | | 1 | Differential coding between current & previous information |
| | | | 2 | Differential coding with frequency detection |
| Conf_Encryption_Type | 1 | TBD | — | — |
| Conf_EIRrexmit_Type | 1 | TBD | — | — |

TABLE 2

| Field Name | Size (Octet) | Default Value | Meaning | |
|---|---|---|---|---|
| Common Message Header included | | | | |
| Flag_CRC_Enabled | 1 | 0 | 0 | Message CRC field disagreed |
| | | | 1 | Message CRC field agreed (CRC field included) |
| Flag_Compression_Enabled | 1 | 0 | 0 | Compression of sensing information disagreed |
| | | | 1 | Compression of sensing information agreed (EIcomp activated) |
| Flag_Encryption_Enabled | 1 | 0 | 0 | Encryption of sensing information disagreed |
| | | | 1 | Encryption of sensing information agreed (EIcipher activated) |

TABLE 2-continued

| Field Name | Size (Octet) | Default Value | Meaning |
|---|---|---|---|
| Flag_Multiplexer_Enabled | 1 | 0 | 0 Multiplexing of sensing information disagreed<br>1 Multiplexing of sensing information agreed (EImux activated) |
| Flag_Authentication_Enabled | 1 | 0 | 0 Authentication of sensing/mobile device disagreed<br>1 Authentication of sensing/mobile device agreed (EDA activated) |
| Flag_CommonAL_Enabled | 1 | 0 | 0 Common Adaptation Layer disagreed<br>1 Common Adaptation Layer agreed (CAL activated) |
| Flag_EIRrexmit_Enabled | 1 | 0 | 0 Retransmission of sensing information disagreed<br>1 Retransmission of sensing information agreed (Rexmit supported) |
| Conf_Sampling_Interval | 4 | 10 | 10 ms × Conf_Sampling_Interval (Larger than requested interval) |
| Conf_Sampling_Size | 1 | 4 | 3 8 bit/sample<br>4 16 bit/sample (Less than requested size)<br>5 32 bit/sample |
| Conf_AdaptationLayer_Type | 1 | 0 | 0 Blank type agreed (Direct communication between EIR and COL)<br>1 Native Adaptation Layer agreed (NAL activated)<br>2 Internet Adaptation Layer agreed (IAL activated) |
| Conf_Compression_Type | 1 | 0 | 0 Sampled information only type agreed (intra coding)<br>1 Differential coding between current & previous information agreed<br>2 Differential coding with frequency detection agreed |
| Conf_Encryption_Type | 1 | TBD | — — |
| Conf_EIRrexmit_Type | 1 | TBD | — — |

TABLE 3

| Field Name | Size (Octet) | Default Value | Meaning |
|---|---|---|---|
| Common Message Header included | | | |
| Flag_CRC_Enabled | 1 | 0 | 0 Message CRC field disconfirmed<br>1 Message CRC field confirmed (CRC field included) |
| Flag_Compression_Enabled | 1 | 0 | 0 Compression of sensing information disconfirmed<br>1 Compression of sensing information confirmed (EIcomp activated) |
| Flag_Encryption_Enabled | 1 | 0 | 0 Encryption of sensing information disconfirmed<br>1 Encryption of sensing information confirmed (EIcipher activated) |
| Flag_Multiplexer_Enabled | 1 | 0 | 0 Multiplexing of sensing information disconfirmed<br>1 Multiplexing of sensing information confirmed (EImux activated) |
| Flag_Authentication_Enabled | 1 | 0 | 0 Authentication of sensing/mobile device disconfirmed<br>1 Authentication of sensing/mobile device confirmed (EDA activated) |
| Flag_CommonAL_Enabled | 1 | 0 | 0 Common Adaptation Layer disconfirmed<br>1 Common Adaptation Layer confirmed (CAL activated) |
| Flag_EIRrexmit_Enabled | 1 | 0 | 0 Retransmission of sensing information disconfirmed<br>1 Retransmission of sensing information confirmed (Rexmit supported) |
| Conf_Sampling_Interval | 4 | 10 | 10 ms × Conf_Sampling_Interval |
| Conf_Sampling_Size | 1 | 4 | 3 8 bit/sample<br>4 16 bit/sample<br>5 32 bit/sample |
| Conf_AdaptationLayer_Type | 1 | 0 | 0 Blank type confirmed (Direct communication between EIR and COL)<br>1 Native Adaptation Layer confirmed (NAL activated)<br>2 Internet Adaptation Layer confirmed (IAL activated) |
| Conf_Compression_Type | 1 | 0 | 0 Sampled information only type confirmed (intra coding)<br>1 Differential coding between current & previous information confirmed<br>2 Differential coding with frequency detection confirmed |
| Conf_Encryption_Type | 1 | TBD | — — |
| Conf_EIRrexmit_Type | 1 | TBD | — — |

TABLE 4

| Field Name | Size (Octet) | Default Value | Meaning | |
|---|---|---|---|---|
| Message Type | 1 | 0x01 . . . 0x05 | 0x01 | EC_ConnectionEstablishment_Request |
| | | | 0x02 | EC_ConnectionEstablishment_Response |
| | | | 0x03 | EC_ConnectionEstablishment_Confirm |
| | | | 0x04 | EC_SensingInformation_Transfer |
| | | | 0x05 | EC_ConnectionRelease_Request |
| Message Sequence | 1 | 0x00 . . . 0xFF | | Message sequence number |
| Message Option | 1 | Bitmap (abcdRRRR) | a | CRC is included (1) or not (0) |
| | | | b | Ciphered message (1) or not (0) |
| | | | c | Compressed message (1) or not (0) |
| | | | d | Retransmitted message (1) or not (0) |
| | | | R | Reserved |

Referring to Tables 1 to 3, the EC_ConnectionEstablishment_Request message, the EC_ConnectionEstablishment_Response message, and the EC_ConnectionEstablishment_Confirm message include a Flag_CRC_Enabled field, a Flag Compresseion Enabled field, a Flag_Encryption_Enabled field, a Flag_Multiplexer_Enabled field, a Flag_Authentication_Enabled field, a Flag_Common-AL_Enabled field, and a Flag_EIRrexmit_Enabled field. Moreover, the EC_ConnectionEstablishment_Request message, the EC_ConnectionEstablishment_Response message, and the EC_ConnectionEstablishment_Confirm message further include system parameter information on protocol operations. The system parameter information includes a Conf_Sampling_Interval field, a Conf_Sampling_Size field, a Conf_AdaptationLayer_Type field, a Conf_Compression_Type field, a Conf_Encryption_Type field, and a Conf EIRrezmit Type field.

The Flag_CRC_Enabled field indicates whether a cyclic redundancy check (CRC) field for error detection is enabled. The Flag Compresseion Enabled field indicates whether a compression technique is enabled for reducing the amount of information in emotion communication. The Flag_Encryption_Enabled field indicates whether an encryption technique is enabled for information protection in emotion communication. The Flag_Multiplexer_Enabled field indicates whether multiplexing of a plurality of information is supported. The Flag_Authentication_Enabled field indicates whether a protocol for emotion communication can perform authentication between the emotion signal sensing device and the emotion service providing device. The Flag_Common-AL_Enabled field indicates whether a CAL layer is enabled for abstracting a communication function. The Flag_EIRrexmit_Enabled field indicates whether retransmission is enabled in the event of an error during an emotion communication process.

The Conf_Sampling_Interval field indicates a sampling interval in the emotion signal sensing device. A value of the corresponding field may be represented by a positive integer, and is obtained by internally multiplying a unit time of 10 ms. The Conf_Sampling_Size field indicates the size of a sample value of an emotion signal, and the sample value is defined by 8/16/32 bits. The Conf_AdaptationLayer_Type field indicates whether each block in the ECAL 320 is supported. The Conf_Compression_Type field indicates an emotion signal compression type. The Conf_EIRrexmit_Type field indicates an emotion signal retransmission type.

Referring to Table 4, the common header includes a message type field, a message sequence field, and a message option field. The message type field tells what type of message the corresponding message is. For example, if the message type field is 0x01, the corresponding message is an EC_ConnectionEstablishment_Request message, and if the message type field is 0x02, the corresponding message is an EC_ConnectionEstablishment_Response message. The message sequence field indicates the number of transmissions of the corresponding message. For instance, a value of the field may increase by 1 each time the same message is transmitted. The message option field notifies in case of additional processing of the corresponding message. The message option field is represented by a bitmap of 1 octet. The first 4 bits of the bitmap of 1 octet are used, and the last 4 bits are reserved. The first 4 bits have a value of 0 or 1, and can be used to identify whether a CRC field for error detection is included or not, whether the message is a ciphered message or not, whether the message is a compressed message or not, and whether the message is a retransmitted message.

The common header of Table 4 can be applied to all messages in this specification, as well as to the EC_ConnectionEstablishment_Request message, the EC_ConnectionEstablishment_Response message, and the EC_ConnectionEstablishment_Confirm message illustrated in Tables 1 to 3. The fields shown in Tables 1 to 4 are provided for illustrative purposes only, and certain fields may be omitted or added.

Figure 6:
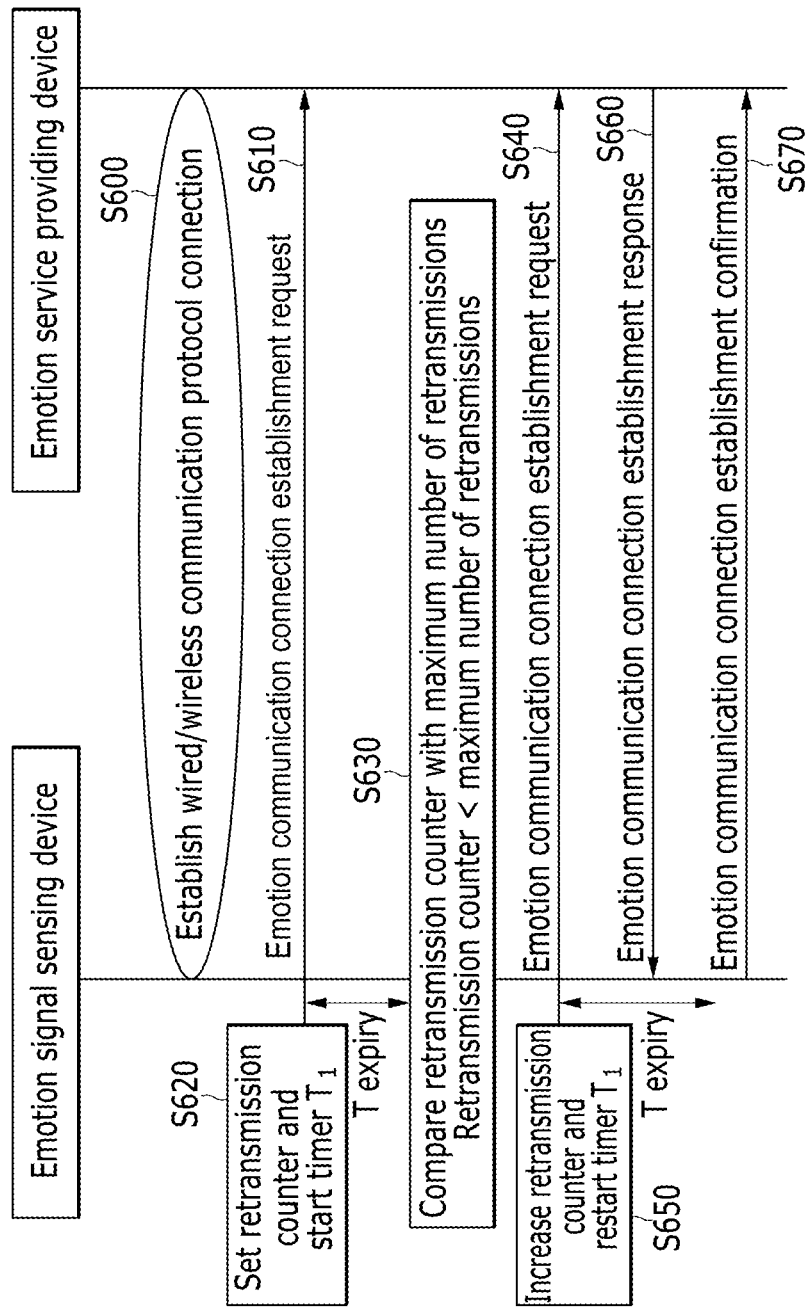
FIG. 6 is a flowchart showing a method of establishing an emotion communication connection between an emotion signal sensing device and an emotion service providing device according to another exemplary embodiment of the present invention.

FIG. 6 is a flowchart showing a method of establishing an emotion communication connection between an emotion signal sensing device and an emotion service providing device according to another exemplary embodiment of the present invention. A case where a retrial is made because of an error occurring in establishing an emotion communication connection between the emotion signal sensing device and the emotion service providing device is illustrated.

Referring to FIG. 6, a protocol connection is established for wireless communication in a general physical layer between the emotion signal sensing device and the emotion service providing device (S600).

The emotion signal sensing device transmits an EC_ConnectionEstablishment_Request message to the emotion service providing device (S610), sets a retransmission counter C, and starts a timer T1 (S620). Here, the retransmission counter C is a counter used to determine whether to retransmit the EC_ConnectionEstablishment_Request message, and an initial setting value $C_0$ may be 1.

If the emotion signal sensing device has not received an EC_ConnectionEstablishment_Response message from the emotion service providing device until expiry of the timer T1, the emotion signal sensing device compares the retransmission counter C with a maximum number of retransmissions $N_{max}$ (S630).

If the retransmission counter is less than the maximum number of retransmissions, the emotion signal sensing device retransmits the EC_ConnectionEstablishment_Request message to the emotion service providing device (S640), increases the retransmission counter by 1, and restarts the timer T1 (S650).

If the emotion signal sensing device receives an EC_ConnectionEstablishment_Response message from the emotion service providing device before expiry of the timer T (S660), the emotion signal sensing device stops the timer T1 and transmits an EC_ConnectionEstablishment_Confirm message to the emotion service providing device (S670).

Meanwhile, in the case that the emotion service providing device has transmitted the EC_ConnectionEstablishment_Response message to the emotion service providing device, the emotion service providing device sets the retransmission counter C and starts the timer T1. If the EC_ConnectionEstablishment_Confirm message has not been received until expiry of the timer T1, the EC_ConnectionEstablishment_Response message can be retransmitted.

Table 5 is one example of a protocol for the timer T1, Table 6 is one example of a protocol for the retransmission counter, and Table 7 is one example of a protocol for the maximum number of retransmissions.

TABLE 5

| Timer | Purpose | Default value |
|---|---|---|
| T1 | Check whether to retransmit message for emotion communication connection establishment | TBD (To be determined) |

TABLE 6

| counter | Purpose | Default value |
|---|---|---|
| C | Counter for retransmission of message for emotion communication connection establishment | TBD |

TABLE 7

| Maximum number of retransmissions | Purpose | Default value |
|---|---|---|
| $N_{max}$ | Maximum number of message retransmissions | TBD |

Figure 7:
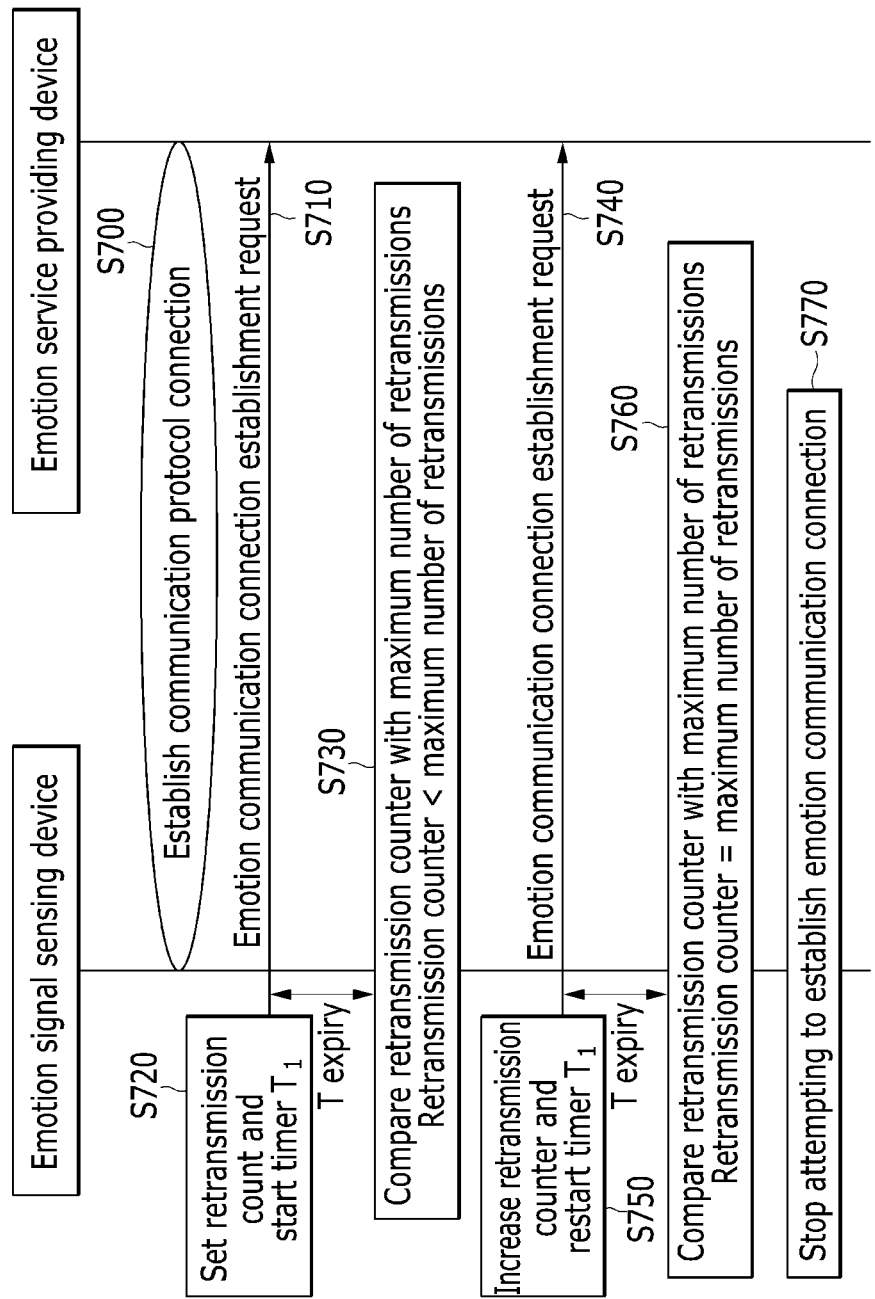
FIG. 7 is a flowchart showing a method of establishing an emotion communication connection between an emotion signal sensing device and an emotion service providing device according to another exemplary embodiment of the present invention.

FIG. 7 is a flowchart showing a method of establishing an emotion communication connection between an emotion signal sensing device and an emotion service providing device according to another exemplary embodiment of the present invention. A case where there is no response from the other party because of repeated errors when an emotion communication connection is established between the emotion signal sensing device and the emotion service providing device is illustrated.

Referring to FIG. 7, a protocol connection is established for wireless communication in a general physical layer between the emotion signal sensing device and the emotion service providing device (S700).

The emotion signal sensing device transmits an EC_ConnectionEstablishment_Request message to the emotion service providing device (S710), sets a retransmission counter C, and starts a timer T1 (S720). If the emotion signal sensing device has not received an EC_ConnectionEstablishment_Response message from the emotion service providing device until expiry of the timer T1, the emotion signal sensing device compares the retransmission counter C with a maximum number of retransmissions (S730). If the retransmission counter is less than the maximum number of retransmissions, the emotion signal sensing device retransmits the EC_ConnectionEstablishment_Request message to the emotion service providing device (S740), increases the retransmission counter by 1, and restarts the timer T1 (S750).

If the emotion signal sensing device has not received an EC_ConnectionEstablishment_Response message from the emotion service providing device until expiry of the restarted timer T1, the emotion signal sensing device compares the retransmission counter C with the maximum number of retransmissions (S760). If the retransmission counter and the maximum number of retransmissions are equal, the emotion signal sensing device stops attempting to establish an emotion communication connection with the emotion service providing device (S770). If the emotion signal sensing device has not received an EC_ConnectionEstablishment_Response message even though it has transmitted the EC_ConnectionEstablishment_Request message a predetermined maximum number of retransmissions, the emotion signal sensing device may determine that the communication state between the emotion signal sensing device and the emotion service providing device is not good, and stops attempting to establish a connection.

Figure 8:
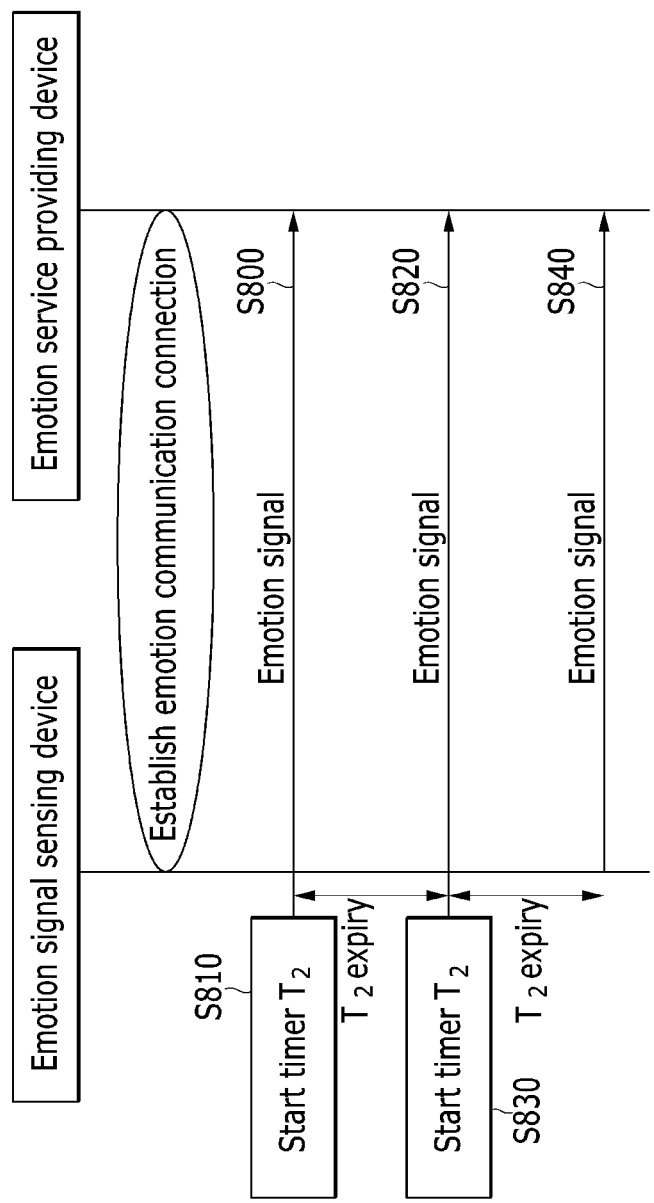
FIG. 8 is a flowchart showing a method of transmitting and receiving an emotion signal sensing device and an emotion service providing device according to one exemplary embodiment of the present invention.

FIG. 8 is a flowchart showing a method of transmitting and receiving an emotion signal and/or emotion information between an emotion signal sensing device and an emotion service providing device according to one exemplary embodiment of the present invention. It is assumed that an emotion communication connection is established between the emotion signal sensing device and the emotion service providing device.

Referring to FIG. 8, the emotion signal sensing device transmits an emotion signal and/or emotion information (EC_SensingInformation_Transfer) of a user to the emotion service providing device (S800), and starts a timer T2 (S810). The timer T2 represents a period during which the emotion signal sensing device transmits an emotion signal and/or emotion information to the emotion service providing device. The period of transmission of an emotion signal and/or emotion information can be defined by an agreement between the emotion signal sensing device and the emotion service providing device in an emotion communication connection establishment process. Table 8 is one example of a protocol that represents the timer T2.

TABLE 8

| Timer | Purpose | Default value |
|---|---|---|
| T2 | Emotion signal transmission period | TBD |

Upon expiry of the timer T2, the emotion signal sensing device retransmits the emotion signal and/or emotion information to the emotion service providing device (S820), and restarts the timer T2 (S830). The emotion signal and/or emotion information transmitted in step S820 may or may not be equal to the emotion signal and/or emotion information transmitted in step S810. According to the settings of the timer T2, the emotion signal and/or emotion information may be periodically transmitted.

Table 9 is one example of a protocol that represents an emotion signal and/or emotion information (EC_SensingInformation_Transfer).

TABLE 9

| Field Name | Size (Octet) | Default Value | Meaning |
|---|---|---|---|
| Common Message Header included | | | |
| Sensing Information Type | 1 | X | Ref[#2] |
| Sensing information Port | 1 | X | Number of port for the sensing information |
| Length | 4 | X | Size of sampled sensing information |
| Sensing Information [0] | Ref[#1] | X | Sampled sensing information |
| ... | | | |
| Sensing Information [Length] | Ref[#1] | X | Sampled sensing information |
| Continued Flag | 0/1 | X | Continued Sensing Information Type is included (1) or Not (0) |

Ref[#1]: Value of 'Conf_Sampling_Size' of Configuration Information
Ref[#2]: Refer protocol constants (e.g. PPG, ECG)

Referring to Table 9, the emotion signal and/or emotion information includes a sensing information type field, a sensing information port field, a length field, a sensing information [ ] field, and a continued flag field.

The sensing information type field tells what type the corresponding emotion signal and/or emotion information is. For instance, the sensing information type field tells whether the corresponding emotion signal and/or emotion information is sensed by PPG or EGG. The sensing information port field is an identifier that identifies the corresponding emotion signal and/or emotion information when a plurality of emotion signals and/or emotion information of the same type are extracted. The length field indicates the size of an emotion signal and/or emotion information. The length field has a size of 4 octets, and is set to a positive integer value. The sensing information field is a field that indicates a format in which values of an emotion signal and/or emotion information are actually stored. Each of the values is defined by the size of a sample value agreed between the emotion signal sensing device and the emotion service providing device at the time of emotion communication connection establishment of FIGS. 5 to 7.

The continued flag field is a field that tells whether another emotion signal and/or emotion information is additionally included in the case of transmission of a plurality of emotion signals and/or emotion information in a single message. If the corresponding field is set to 1, this means that there is additional information, and if the corresponding field is set to 0, this means that the corresponding message ends with no additional information to follow.

Figure 9:
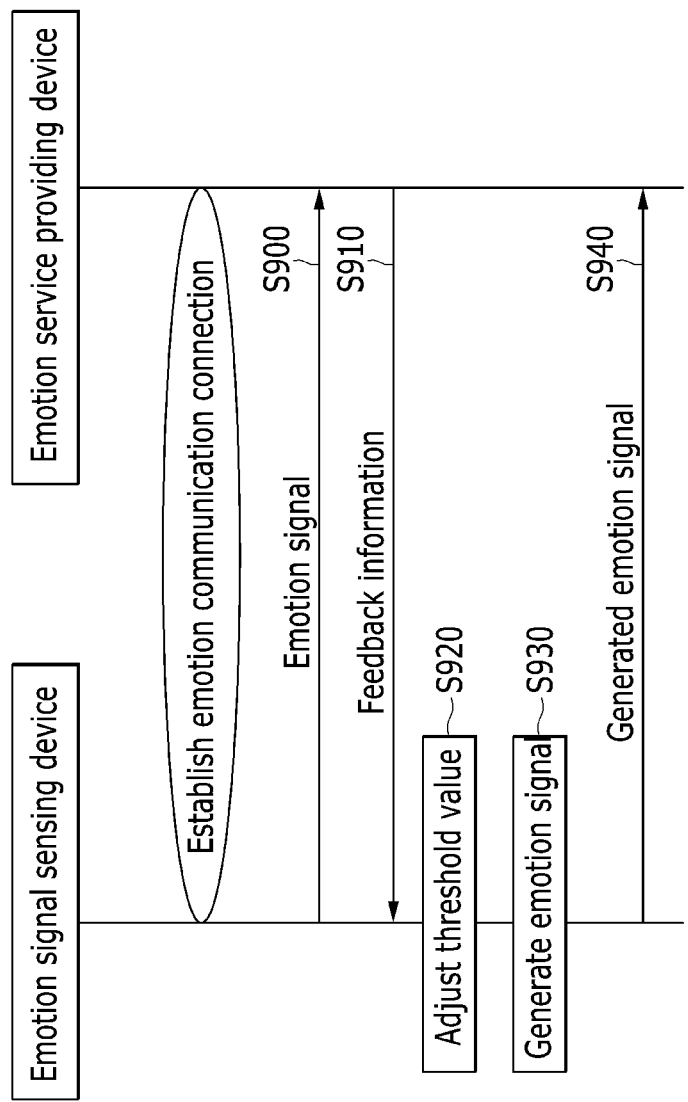
FIG. 9 is a flowchart showing a method of transmitting and receiving an emotion signal sensing device and an emotion service providing device according to another exemplary embodiment of the present invention.

FIG. 9 is a flowchart showing a method of transmitting and receiving an emotion signal sensing device and an emotion service providing device according to another exemplary embodiment of the present invention. It is assumed that an emotion communication connection is established between the emotion signal sensing device and the emotion service providing device.

Referring to FIG. 9, the emotion signal sensing device transmits an emotion signal and/or emotion information (EC_SensingInformation_Transfer) of a user to the emotion service providing device (S900).

The emotion service providing device transmits feedback information to the emotion signal sensing device (S910). The feedback information may be judgment information on the accuracy of the emotion signal and/or emotion information that the emotion service providing device has received from the emotion signal sensing device. For example, the emotion service providing device can judge the accuracy of the emotion signal and/or emotion information based on reactions of the user to be provided with an emotion service and/or information received from the emotion signal sensing device, and give feedback of information on the accuracy to the emotion signal sensing device. In one example, if the user to be provided with an emotion service refuses to receive the emotion service within a predetermined time from a point of time when the emotion service is provided, the emotion service providing device can determine that there is an error in the accuracy of the emotion signal and/or emotion information of the emotion signal sensing device and give notice of this determination. In another example, if the rise and fall of a plurality of emotion signals and/or emotion information received within a predetermined time from the emotion signal sensing device exceeds a reference range, the emotion service providing device can determine that there is an error in the accuracy of the emotion signals and/or emotion information of the emotion signal sensing device and give notice of this determination. The feedback information may further include feedback information on the intensity of an emotion signal, the period of an emotion signal, etc.

The emotion signal sensing device adjusts a threshold value for generating an emotion signal and/or emotion information based on feedback information (S920). That is, the emotion signal sensing device uses a preset threshold value in order to extract an emotion signal and/or emotion information from a signal sensed by a sensor. By adjusting the threshold value based on feedback information received from the emotion service providing device, the emotion signal sensing device can transmit an accurate emotion signal and/or emotion information.

The emotion signal sensing device generates an emotion signal based on the threshold value adjusted in step S920 (S930), and transmits the generated emotion signal to the emotion service providing device (S940).

Figure 10:
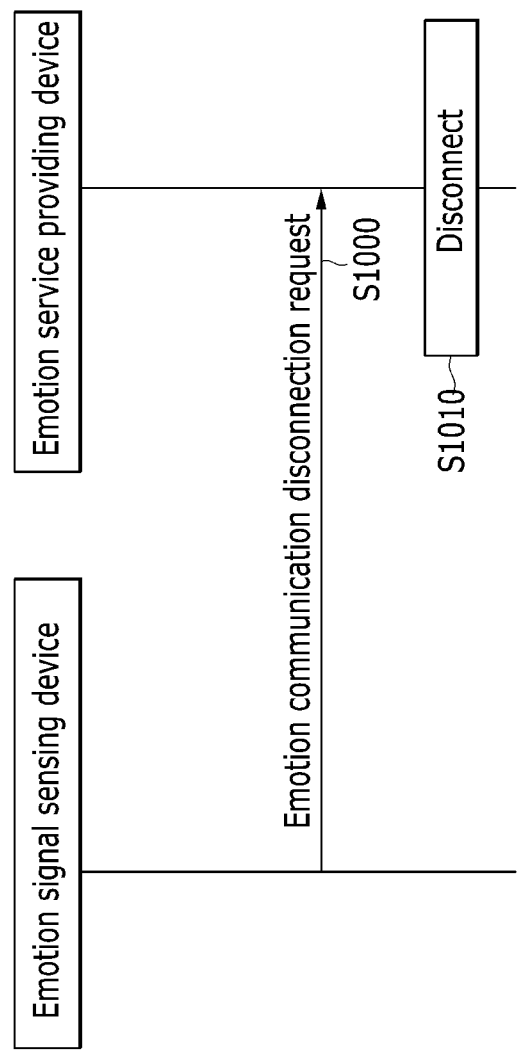
FIGS. 10 and 11 are flowcharts showing a method of terminating emotion communication between an emotion signal sensing device and an emotion service providing device according to one exemplary embodiment of the present invention.
Figure 11:
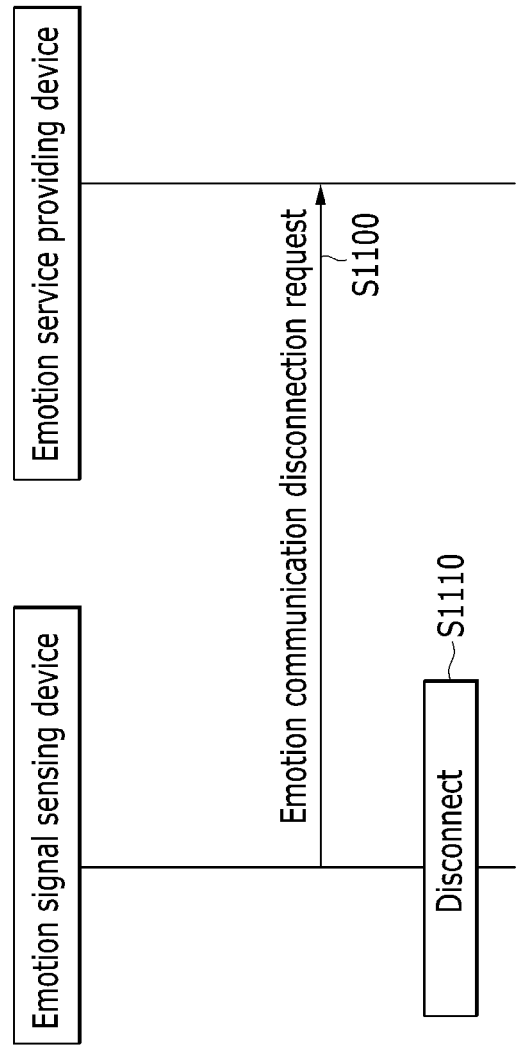

FIGS. 10 and 11 are flowcharts showing a method of terminating an emotion communication between an emotion signal sensing device and an emotion service providing device according to one exemplary embodiment of the present invention.

Referring to FIG. 10, the emotion signal sensing device transmits an emotion communication disconnection request message to the emotion service providing device (S1000). Having received the emotion communication disconnection request message, the emotion service providing device terminates the connection with the emotion signal sensing device (S1010).

Referring to FIG. 11, the emotion service providing device transmits an emotion communication disconnection request message to the emotion signal sensing device (S1100). Having received the emotion communication disconnection request message, the emotion service providing device terminates the connection with the emotion signal sensing device (S1110).

In FIGS. 10 and 11, the emotion communication disconnection request message may contain the reason for terminating the connection. Table 10 is one example of the emotion communication disconnection request message.

TABLE 10

| Field Name | Size (Octet) | Default Value | Meaning | |
|---|---|---|---|---|
| Common Message Header Included | | | | |
| Reason | 1 | 0 | 0 | Normal Reason |
| | | | 1 | Reserved |

There is proposed a method for emotion signal transmission and reception between an emotion signal sensing device and an emotion service providing device. Therefore, a user can be provided with an emotion-based service desired by the user.

The exemplary embodiments of the present invention described above are implemented not only by a device and a method, but they may be implemented by a program for executing the functions corresponding to the configuration of the exemplary embodiment of the present invention or a recording medium having the program recorded thereon.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for emotion communication of an emotion signal sensing device that senses a user's emotions, the method comprising:
   sensing biological and environmental information of the user by an emotion signal sensing device;
   generating an emotion signal of the user based on the biological and environmental information;
   establishing a wireless emotion communication connection with an emotion service providing device, the emotion service providing device being distinct from the emotion signal sensing device and providing the emotion service to the user based on the emotion signal; and
   transmitting the emotion signal to the emotion service providing device via the established emotion communication connection,
   wherein the emotion signal sensing device includes:
   a sensing signal processor processing the biological and environmental information sensed from the user;
   an emotion signal processor generating the emotion signal using the biological and environmental information processed by the sensing signal processor, and compensating for errors in the emotion signal when the emotion signal has errors; and
   an emotion signal communicator establishing the wireless emotion communication connection with the emotion service providing device,
   wherein the emotion signal sensing device performs emotion communication with the emotion service providing device using a protocol layer that is implemented by the emotion signal communicator,
   wherein the protocol layer comprises:
   a first layer that processes the emotion signal transferred from the emotion signal processor;
   a second layer that receives the processed emotion signal from the first layer, and transmits the processed emotion signal to the emotion service providing device; and
   a protocol management plane that manages profile information of a first protocol for transmitting the processed emotion signal to the emotion service providing device and a second protocol for establishing a connection between the emotion signal sensing device and the emotion service providing device.

2. The method of claim 1, wherein the generating of an emotion signal comprises:
   setting a threshold value;
   extracting a signal having a greater value than the threshold value from among the biological information; and
   forming the emotion signal from the extracted signal.

3. The method of claim 2, further comprising:
   receiving feedback information of the emotion signal from the emotion service providing device; and
   controlling the threshold value based on the feedback information.

4. The method of claim 1, wherein the establishing of an emotion communication connection comprises:
   transmitting a first message requesting an emotion communication connection establishment to the emotion service providing device;
   receiving a second message from the emotion service providing device in response to the first message; and
   transmitting a third message to the emotion service providing device in response to the second message.

5. The method of claim 4, wherein the first message contains a list of functions supported by the emotion signal sensing device, and the second message contains information on a function selected from the list of the functions by the emotion service providing device.

6. The method of claim 4, wherein the establishing of an emotion communication connection comprises retransmitting the first message a predetermined number of times before receiving the second message from the emotion service providing device.

7. The method of claim 6, wherein the retransmitting comprises:
   starting a timer after transmitting the first message; and
   if the second message is not received until expiry of the timer, retransmitting the first message.

8. The method of claim 1, wherein the transmitting of the emotion signal comprises periodically transmitting the emotion signal.

9. The method of claim 1, further comprising:
   transmitting a message containing the reason for releasing the connection to the emotion service providing device; and
   releasing the connection with the emotion service providing device.

* * * * *